United States Patent [19]

Thompson

[11] 4,175,034
[45] Nov. 20, 1979

[54] CLOSED-LOOP VACUUM FRACTIONATION PROCESS

[75] Inventor: H. Lytle Thompson, Park Ridge, Ill.

[73] Assignee: UOP Inc., Des Plaines, Ill.

[21] Appl. No.: 949,606

[22] Filed: Oct. 10, 1978

[51] Int. Cl.² .......................... B01D 3/10; C10G 7/00; C10G 21/28
[52] U.S. Cl. ........................ 208/321; 203/87; 203/92; 203/94; 203/96; 203/97; 208/356; 208/357
[58] Field of Search ............... 203/87, 92, 94, 96, 203/97, 93; 208/321, 356, 357

[56] References Cited

U.S. PATENT DOCUMENTS

| | | | |
|---|---|---|---|
| 2,224,925 | 12/1940 | Potts et al. | 203/87 |
| 2,462,013 | 2/1949 | Waterman | 203/87 |
| 3,413,217 | 11/1968 | Kunesh | 208/356 |
| 3,471,371 | 10/1969 | Nagy et al. | 203/96 |
| 4,083,772 | 4/1978 | Asselin et al. | 208/321 |

Primary Examiner—Herbert Levine
Attorney, Agent, or Firm—James R. Hoatson, Jr.; John F. Spears, Jr.; William H. Page, II

[57] ABSTRACT

A fractionation process wherein a fractionation column is maintained at a subatmospheric pressure through the use of a steam-jet ejector. Water drawn off the overhead receiver of the fractionation column is vaporized by indirect heat exchange to form the moderate pressure steam charged to the ejector. The effluent of the ejector is passed through a condenser, and the resultant condensate is recycled to the overhead receiver by admixture with the overhead vapor stream of the fractionation column. The disposal of hydrocarbon-contaminated aqueous overhead liquid is thereby minimized.

7 Claims, 1 Drawing Figure

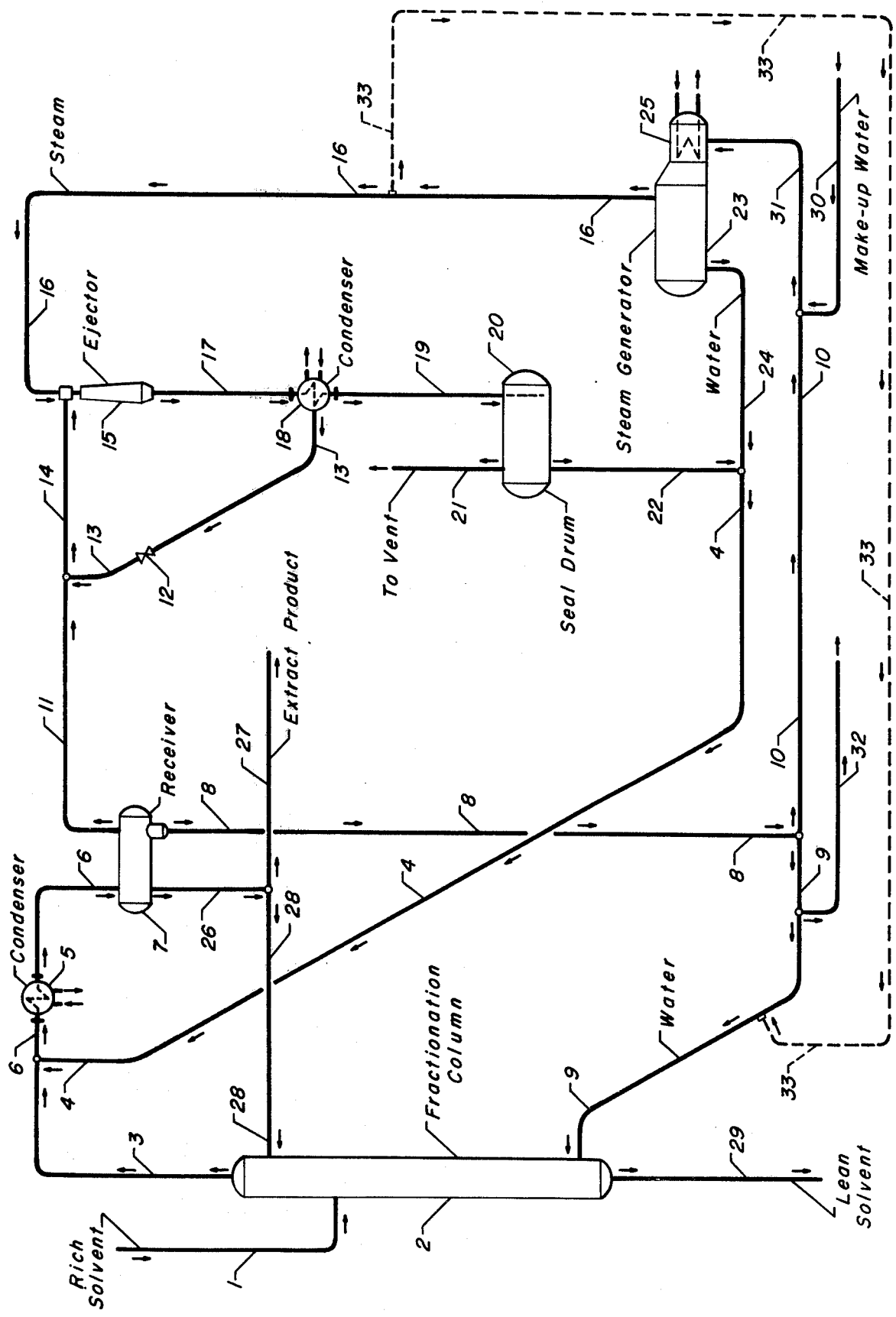

CLOSED-LOOP VACUUM FRACTIONATION PROCESS

FIELD OF THE INVENTION

The invention relates to a method or process for fractionating a water-containing mixture of hydrocarbonaceous chemical compounds at a subatmospheric pressure. The invention therefore relates to a process for the separation of aromatic hydrocarbons and other petroleum-derived materials by fractionation. The invention also relates to a process for the fractionation of hydrocarbonaceous chemical compounds in which water vapor is present in the generated overhead vapors and is subsequently condensed, as is common to many steam distillation operations. References concerned with similar subject matter may be found in Classes 203 and 208.

PRIOR ART

The subatmospheric pressure fractionation of hydrocarbons and other chemicals is a very important step in many commercial processes in the petroleum, petrochemical and chemical industries. It has therefore received a considerable amount of attention and has become a well-developed art. In many instances, the subatmospheric pressure is maintained by withdrawing uncondensed vapors from the overhead receiver of the fractionation column. These uncondensed vapors are pulled into a vacuum source or pump, which often is a steam jet ejector. It is often a common practice to pass the effluent of the ejector into a condensing zone wherein substantially all of the water vapor in the effluent is condensed.

A subatmospheric fractionation process is described in U.S. Pat. No. 3,413,217 (Cl. 208-356) issued to J. G. Kunesh. Steam is introduced into a lower portion of the column at a controlled variable rate. The overhead vapor stream removed from the column is passed through an overhead condenser and then into an overhead receiver. A hydrocarbon stream removed from the receiver is divided into a product stream and reflux liquid. An aqueous condensate stream is also removed from the overhead receiver and is passed into a steam generation zone wherein it is vaporized by indirect heat exchange. One portion of this steam is used as the steam charged to the lower portion of the fractionation column and the remainder of the steam is passed out of the process, as to a refinery steam system. U.S. Pat. No. 3,471,371 (Cl. 203-96) issued to R. L. Nagy is also pertinent as it teaches the use of aqueous overhead condensate as a source of steam fed to the bottom of a fractionation column.

The inventive concept is preferably applied to a liquid-liquid extraction process for the production of aromatic hydrocarbons such as that shown in U.S. Pat. No. 3,492,222 (Cl. 208-321) issued to H. M. VanTassell. This reference also shows the removal of an aqueous condensate from the overhead receiver of the extract recovery column and the passage of the condensate through a steam generator. The resultant steam is passed into the bottom of the extract recovery column to aid in the distillation. U.S. Pat. Nos. 3,642,614 and 3,864,244 (both Cl. 208-321) issued to H. M. VanTassell also describe liquid-liquid extraction processes for the recovery of aromatics. In these processes, a fluid stream comprising a solvent, water and aromatic hydrocarbons is passed into a fractionation column and condensed water is drawn off the overhead receiver associated with this column. In both of these references, the drawn off condensed water is used in part in a water wash column to remove residual amounts of solvent from the raffinate stream produced in the extraction zone.

BRIEF SUMMARY OF THE INVENTION

The invention provides a method of fractionating a mixture of distillable hydrocarbonaceous chemical compounds at a subatmospheric pressure. A steam-jet ejector is utilized to maintain the subatmospheric pressure by pulling uncondensed vapors from the overhead receiver of the fractionation column. Passage of the ejector effluent stream through a condensing zone results in the formation of liquid water containing some of the more volatile chemical compounds in the feed stream passed into the fractionation column. The invention reduces or eliminates the problem of disposing of this contaminated water by internally recycling the water, with the water being returned to the overhead receiver by admixture with the overhead vapor stream of the column at a point upstream of the overhead condenser. The utilization of a steam-jet ejector in subatmospheric fractionation processes is thereby facilitated.

The inventive concept also internally recycles the condensed water drawn off the overhead receiver to thereby further reduce the amount of contaminated water which is discharged from the fractionation process. This relatively clean condensed water is passed through a steam generation zone wherein by indirect heat exchange it is converted into the moderate pressure steam used as the primary or motive stream in the ejector.

DESCRIPTION OF THE DRAWING

The drawing illustrates one of the more limited embodiments of the invention as it may be applied to a liquid-liquid extraction process for the recovery of aromatic hydrocarbons. For simplicity and clarity, a number of pieces of apparatus normally required in the operation of the process have not been shown. This deleted apparatus includes pressure, flow, and temperature control systems, vessel internals, etc., all of which may be of customary design. This depiction of one embodiment of the invention is not intended to exclude from the inventive concept other embodiments set out herein or which are the result of normal and reasonable modification of these embodiments.

Referring now to the drawing, a rich solvent stream comprising a solvent selective for aromatic hydrocarbons, water, and aromatic hydrocarbons enters the process through line 1 and is directed to an intermediate point of a fractionation column 2. This column is maintained at fractionation conditions effective to separate the entering rich solvent into an overhead stream comprising water vapor and vaporized aromatic hydrocarbons which is removed from the column through line 3 and the lean solvent stream comprising the selective solvent which is removed from the fractionation column through line 29.

The overhead vapor stream is admixed with a liquid stream from line 4 which comprises water and dissolved hydrocarbons. This admixture effects a preliminary cooling of the overhead vapor stream, which is then passed through an overhead condenser 5 via line 6. A resultant mixed-phase overhead stream is passed into the overhead receiver 7. The overhead stream is therein separated into an aqueous liquid stream collected in the boot of the receiver and withdrawn in line 8, a less dense liquid-phase aromatic hydrocarbon stream removed in line 26 and a vapor-phase stream removed in line 11. A first portion of the liquid-phase aromatic hydrocarbons is returned to the fractionation column as reflux through line 28 and a second portion is withdrawn from the process as a product stream through line 27.

The fractionation column and the overhead receiver are maintained at a subatmospheric pressure through the use of a jet ejector 15. The suction side of the ejector removes uncondensed hydrocarbons and relatively uncondensable compounds such as nitrogen and carbon dioxide from the overhead receiver through line 11. The motive or primary stream fed to the ejector is moderate pressure steam from line 16, and the effluent of the ejector is removed in line 17. The ejector effluent is passed into a condenser 18 wherein at least a partial condensation is effected by indirect heat exchange against cool water or some other suitable cool fluid. A portion of the ejector effluent stream or the vaporous material remaining after the condensation step may be returned to the suction side of the ejector through line 13 at a rate controlled by valve 12 for the purpose of controlling the operation of the ejector.

The remaining net ejector effluent stream is passed through line 19 into a seal drum 20. The entering net ejector effluent stream comprises liquid-phase water and a small amount of liquid-phase hydrocarbons which remain vaporized after passing through the overhead condenser 5. It also comprises an equilibrium mixture of water vapor and relatively non-condensable light gases such as nitrogen or carbon dioxide and may contain small amounts of gaseous hydrocarbons. The total uncondensed gases are removed from the seal drum through line 21 for disposal through an environmentally acceptable venting system. The liquid-phase material is removed through line 22.

The aqueous overhead condensate collected in the boot of the overhead receiver is removed through line 8. A portion, and possibly all, of this stream is passed into line 10 to be used to generate moderate pressure steam fed to the ejector 15. An optional make-up water stream enters the process through line 30 and the resultant total water stream is fed into a steam generator 23 through line 31 and contacted with heating element 25. Indirect heat exchange of the entering water with a suitable high temperature fluid, such as high pressure steam or a hot oil, results in the vaporization of a major portion of the water and the formation of the moderate pressure steam which is transported in line 16. The unvaporized portion of the water is removed from the steam generator in line 24 and admixed with the liquid stream removed from the seal drum in line 22. The resultant combined water stream is carried by line 4 and is admixed with the overhead vapor stream of the fractionation column.

A second portion of the water removed from the overhead receiver through line 8 is passed into the bottom of the fractionation column after it has been vaporized in a means not shown. A portion of the water stream carried by line 9 may be removed from the process in line 32 to prevent the buildup of certain water-soluble compounds within the process or to remove excess water entering the process with the rich solvent stream.

An alternative method of operation of the process comprises the diversion of a portion of the moderate pressure steam formed in the steam generator 23 through line 33. This steam may then be passed directly into the bottom of the fractionation column 2 to supply all or a portion of the steam fed to this column. The rate of flow of the steam in line 33 may be sufficient to provide the total heat input required at the bottom of the fractionation column.

DETAILED DESCRIPTION

Fractionation is a well developed art which has been thoroughly described in many references. Those skilled in the art are therefore well versed in the design and operation of fractionation systems and may successfully adjust to the practice of the subject invention with a minimum of guidance. The discussion of basic and well known fractionation steps in the subject process will accordingly be held to a minimum, and the invention will be discussed primarily in terms of its application to a liquid-liquid extraction operation for the recovery of aromatic hydrocarbons.

It is often desired to operate a fractionation column at a subatmospheric pressure. Normally, this is because the compounds being fractionated either have a very low vapor pressure or are sensitive to elevated temperatures which would be required to effect their vaporization. Reduced crude oil fractions are an example of the former situation and olefinic aromatic hydrocarbon monomers, such as styrene, are an example of the latter. Unless otherwise specified, all references herein to the pressure maintained within a fractionation column refer to the pressure at the top of the column.

Another method of fractionating a mixture of temperature-sensitive compounds involves the passage of steam into a lower portion of a fractionation column and is referred to as steam distillation. This fractionating method may also be used for compounds which are not temperature-sensitive. The rate of steam addition to the bottom of the column may vary from a small amount which merely assists the separation to the large amount necessary to supply all of the heat input required to perform the fractionation, thereby eliminating the need for a reboiler. This steam migrates upward through the fractionation column and normally is condensed in the overhead system simultaneously with any water present in the feed stream. The resultant condensate is removed as a denser liquid phase which settles to the boot of the overhead receiver. This water will have dissolved in it an equilibrium concentration of the other compounds present in the overhead receiver, and therefore may present serious effluent disposal problems.

A subatmospheric pressure in a fractionation column is normally maintained by connecting a vacuum source to the overhead receiver into which the overhead vapor stream is directed. This vacuum source may be a mechanical vacuum pump, but is very often a jet-ejector. When steam is used as the motive or high pressure stream charged to an ejector, it is referred to as a steam-jet ejector. These devices are in widespread use and are amply described in the literature. For instance, steam-jet ejectors are described at pages 6–29 to 6–32 of the Fourth Edition of *Perry's Chemical Engineers' Handbook* (1963), McGraw-Hill Book Co.

The effluent stream of the ejectors is often passed through a cooler which condenses the steam and possibly some of the educted material. The purpose of this may be to reclaim the resultant condensate or to prevent the discharge of the uncondensed steam. An interstage condenser is sometimes used between two ejectors operated in series to reduce the load on the following stage, thus reducing the consumption of the motive vapor and the required ejector size.

Besides being effective vacuum pumps, steam-jet ejectors are also very effective mixing devices. The effluent of the ejector is therefore a well-mixed blend of the vapors removed from the overhead receiver and the steam charged to the ejector. The result, therefore, of passing the ejector effluent through a condenser is the production of liquid-phase water which contains a variable, but significant amount of the hydrocarbons or other distillable compounds present in the vapors found in the overhead receiver. That is, hydrocarbons will be present as a contaminant in both the aqueous condensate removed from the overhead receiver and the aqueous condensate produced by cooling the ejector effluent stream. A separate liquid phase which predominates in these other compounds may also be formed if they are present in large enough quantities.

The disposal of contaminated water in an environmentally acceptable manner requires its purification and may be very costly. The use of a steam-jet ejector during steam distillation therefore creates a condensate disposal problem, which may be of considerable magnitude on large fractionation systems or in situations in which the feed stream to the fractionation column contains a large amount of volatile compounds. The problem of disposing of contaminated aqueous condensates is often complicated by the fact that using the condensate at another location will merely transfer the contaminants into another process stream.

It is an objective of the present invention to provide a subatmospheric pressure fractionation process which facilitates the use of a steam-jet ejector and which has minimal contaminated water discharge problems. It is another objective of the invention to provide a method of fractionating a feed stream comprising water, a solvent selective for aromatic hydrocarbons and aromatic hydrocarbons at a subatmospheric pressure.

The subject invention may be applied to many liquid-liquid extraction processes for the separation of hydrocarbons. These processes are understood by those skilled in the art and have been well documented, as is shown by the previously cited references. A brief description of extraction processes used to recover aromatic hydrocarbons will nevertheless be presented in order to provide a background for describing the invention.

These liquid-liquid extraction processes referred to herein comprise an initial contacting step in which a lean solvent stream is contacted with a hydrocarbon feed stream comprising aromatic and non-aromatic hydrocarbons in an extraction zone. The extraction zone may comprise a tower containing suitable packing such as Berl Saddles or Raschig Rings, or a tower containing suitable perforated trays, or a rotating disk contractor (RDC). The feed stream is contacted therein with the lean solvent, preferably by countercurrent multi-stage contacting, at conditions effective to produce a raffinate stream which comprises the feed stream minus the extracted aromatic hydrocarbons and an aromatic-rich solvent stream. The rich solvent stream may also be referred to as the extract stream. The feed stream may be a naphtha, a reformate or a fractionated reformate which contains the desired aromatic hydrocarbons. Preferably, the feed stream has an aromatic hydrocarbon concentration above 20 mole percent. Typical feed streams are formed by stabilizing a reformate or by fractionating a reformate to yield a $C_6$ to $C_8$ cut comprising benzene, toluene, xylenes, ethylbenzene and $C_6$ to $C_8$ paraffins.

A wide variety of aromatic hydrocarbon-selective solvents may be used in the extraction step. These include diethylene glycol, polyethylene glycol, dipropylene glycol, various polypropylene glycols, dimethylsulfoxide, n-methyl pyrrolidone, morpholine, etc. A preferred solvent is one of the sulfolane-type which may be characterized as having a five-membered ring structure containing one sulfur atom and four carbon atoms with two oxygen atoms bonded to the sulfur atom. More preferably, two hydrogen atoms are bonded to each carbon atom. A specific example of a sulfolane-type solvent is tetrahydrothiophene 1,1, dioxide.

The solvent composition utilized in aromatic hydrocarbon extraction processes often comprises a mixture of water and one or more of the solvents listed herein. This is especially true when a sulfolane-type solvent is used as it provides several processing benefits. These normally include an increased selectivity for aromatic hydrocarbons, resulting from a decrease in the solubility of the hydrocarbons in the solvent mixture, and the presence of a relatively volatile material in the downstream fractionation system. The water content of the solvent mixture is beneficial in the fractionation system since the steam formed by its partial vaporization aids in stripping non-aromatic hydrocarbons out of the aromatic-rich solvent and in subsequently stripping the extracted aromatic hydrocarbons from the solvent.

The concentration of water in the solvent stream fed to the extraction zone may range from about 0.1 to about 20.0 wt.%. When a sulfolane-type solvent is utilized, the water concentration is preferably between 0.1 and 1.0 wt.%. If a polyalkylene glycol solvent is used, the water is preferably between 6 and 15 wt.%. At least a portion of this water becomes vaporized during the recovery of the extracted aromatic hydrocarbons from the purified rich solvent in the low pressure fractionation column described below. The resulting water vapor forms part of the overhead vapor stream removed from this fractionation column and is partially condensed to form liquid-phase water collected in the boot of the overhead receiver associated with this column. The non-condensables along with equilibrium water and hydrocarbon vapor are removed from the overhead receiver by the vacuum source and are normally subjected to a second condensation step which forms a second aqueous phase containing dissolved hydrocarbons.

The inventive concept utilizes at least a portion of the liquid-phase water collected in this fractionation column in a steam generator which provides the steam used in the jet-ejector and in the fractionation column. The second aqueous phase formed by the condensation of the ejector effluent is also recycled internally, but it is directed into the overhead receiver, preferably by admixture into the overhead stream of the fractionation column. This admixture step should reduce the cooling required in the overhead condenser thus reducing the utilities cost of operating the process. The recycled second aqueous phase may be admixed with the overhead vapor stream of the fractionation column either upstream or downstream of the overhead condenser, with the preferred location being dependent on such factors as the temperature of the aqueous phase.

Water will be continuously added to the closed loop water vapor recycle system described herein because of the vaporization of water present in the rich solvent stream fed to the fractionation column. It is expected that the rate of water addition from this source will exceed the rate of water loss in the lean solvent, extract product, and vent gas streams. Water is therefore normally withdrawn from the process at a rate necessary to balance the rates of addition and withdrawal. The rate of this withdrawal will, however, be much less than the total rate at which water is condensed in the process and does not conflict with the objectives of the invention. The withdrawn water may be used to replenish the water content of the solvent stream or to remove dissolved solvent from the raffinate stream in a water wash column.

In the preferred liquid-liquid extraction process, the rich solvent stream produced in the extraction zone is passed directly into an extractive stripping or extractive distillation column. The bottoms stream of this stripping column is then passed into the subatmospheric pressure fractionation column, which is often referred to as the aromatics recovery column or the extract recovery column.

The rich solvent stream removed from the liquid-liquid extraction zone will normally contain a small amount of non-aromatic hydrocarbons which are predominantly more volatile than the benzene and/or other aromatic hydrocarbons in the rich solvent stream. These non-aromatic hydrocarbons may be very effectively removed from the solvent stream in the extractive stripping column by a partial stripping of the total hydrocarbon content of the rich solvent stream and are then removed from the extractive stripping column as an overhead stream. This stream may be returned to the extraction zone as reflux for recovery of any aromatic hydrocarbons it contains. The removal of non-aromatic hydrocarbons conducted in the extractive stripping column may be deleted if, as in the production of gasoline blending stocks, the non-aromatic hydrocarbons may be tolerated in the final product stream. An extractive stripping column is normally operated at a pressure of from about 0 to 100 psig. with pressures less than 20 psig. being preferred.

The bottoms stream of the extractive stripping column comprises the solvent, water and aromatic hydrocarbons and is essentially free of non-aromatic hydrocarbons. This stream is also referred to herein as the rich solvent stream, and it is passed into the aromatic recovery fractionation column. In this second column, the aromatic hydrocarbons are removed from the rich solvent stream. With a sulfolane-type solvent, this separation is quite easy and produces a high purity overhead stream comprising the extracted aromatic hydrocarbons and a lean solvent stream removed as a bottoms product.

Most solvents show some degradation as the result of thermal instability or oxidation. For this reason, it is normal practice to limit the bottom liquid temperatures used in solvent fractionation columns to less than 350° F. in the case of a sulfolane-type solvent and 380° F. when a diethylene glycol solvent system is used. The pressure maintained within the aromatic hydrocarbon recovery column is normally subatmospheric and is preferably about 200 to 500 mm. Hg absolute. The pressure in the overhead receiver of the aromatic hydrocarbon recovery column will be lower to overcome the inherent flow resistance in the overhead system. A column having about thirty valve trays is preferred for use as the aromatic hydrocarbon recovery column.

It is preferred that the overhead vapor stream of the aromatic hydrocarbon recovery column is cooled to a temperature in the range of about 60° F. to 110° F. in the overhead condenser. This should effect the condensation of a very high percentage of the total overhead vapor, which is desirable since any uncondensed material must be removed by the jet ejector. In the preferred extraction process, the overhead vapor stream should contain very little non-condensable gases due to the nature of the feed hydrocarbons and the solvent and because of the separation performed in the upstream extractive stripping column. It will therefore be predominantly aromatic hydrocarbons, such as benzene and xylene, plus a lesser amount of water. The net vapor removed from the overhead receiver will be an approximate equilibrium mixture comprising both the aromatic hydrocarbons and water.

The water condensed in the overhead condenser contains an equilibrium mixture of the hydrocarbons present in the overhead receiver. It is removed as a denser aqueous liquid stream and, according to the inventive concept, internally recycled within the fractionation system associated within the aromatic hydrocarbon recovery column. All or a portion of the aqueous liquid stream is vaporized in a steam generator to form moderate pressure steam used within the fractionation system. By the term "moderate pressure steam," it is intended to refer to steam having a pressure of from 50 to about 250 psig. A second portion of the aqueous liquid stream may be passed into the aromatic hydrocarbon recovery column through the reboiler associated with the column. As another alternative, some of the moderate pressure steam formed from the aqueous liquid stream may be fed into the recovery column.

The steam generator may be of customary design and is operated in accordance with well known operational and safety standards. It preferably comprises a shell and tube indirect heat exchanger in which steam or a similar high temperature fluid is passed through the tubes. Operation in this manner eliminates the direct addition of steam to the fractionationation system, thereby eliminating the problem of purifying or disposing of a corresponding additional quantity of contaminated condensate.

The jet-ejector may be of customary design, and it may be operated according to established practices. The effluent of the ejector is passed into a second condenser. This condenser is preferably operated at a pressure of about 0 to 10 psig. since a positive pressure aids in effecting the condensation. A high degree of condensation is desired in order to reduce the volume of vapor which must be passed to the vent system. The second condenser should therefore cool the ejector effluent to approximately 60° F. to 110° F. A small variable amount of the ejector effluent may be returned to the suction of the ejector for the purpose of controlling the generated vacuum. The remaining net ejector effluent is passed into a seal drum or vapor-liquid separator as a mixed-phase stream, with the effluent entering at a point below the liquid level in the drum to provide the desired vapor seal.

The condensate liquid collected in this seal drum is recycled to the overhead receiver, thereby achieving an objective of the invention through the elimination of a contaminated aqueous effluent stream. This condensate stream will comprise water and the hydrocarbons which are present in the net overhead vapor withdrawn from the overhead receiver. The temperature of this stream will be considerably lower than that of the overhead vapors of the aromatic hydrocarbon recovery column, which may be about 175° F. or higher. Admixture of the relatively cool condensate into the overhead vapor stream effects a direct heat exchange between the two streams and a cooling of the overhead vapor stream. This beneficial result lowers the required cooling capacity of the overhead condenser and is a second advantage of internally recycling the condensate stream. Performing the admixture downstream of the overhead condenser may be preferred if it significantly lowers the fluid flow rate on the hot side of the condenser or if it allows acceptable condenser operation with a higher exit temperature.

In accordance with this description, the preferred embodiment of the invention may be characterized as a method of fractionating a rich solvent stream which comprises the steps of passing a feed stream which comprises a sulfolane-type solvent, water and aromatic hydrocarbons into a fractionation column at an intermediate first point, and removing a first product stream comprising the sulfolane-type solvent from the fractionation column at a second lower point; effecting a partial condensation of an overhead vapor stream comprising water and aromatic hydrocarbons and which is removed from the fractionation column by admixing the overhead vapor stream with a hereinafter specified liquid recycle stream and by passing the overhead vapor stream through a first condensing zone, and passing the resultant mixed-phase stream into an overhead receiver maintained at a subatmospheric pressure; withdrawing an overhead liquid comprising aromatic hydrocarbons and containing less than 10 mole percent water from the overhead receiver, passing a first portion of the overhead liquid into the fractionation column as reflux and removing a second portion of the overhead liquid as a second product stream; passing a first vapor stream comprising water and aromatic hydrocarbons from the overhead receiver to the suction inlet of a steam-jet ejector operated at conditions effective to maintain the subatmospheric pressure in the overhead receiver and thereby forming an ejector effluent stream comprising aromatic hydrocarbons and steam; condensing at least a portion of the ejector effluent stream by passing through a second condensing zone; passing the ejector effluent stream into a vapor-liquid separation zone maintained at conditions effective to separate the ejector effluent stream into a second vapor stream comprising water and a condensate liquid stream comprising water and aromatic hydrocarbons; admixing the condensate liquid stream into the overhead vapor stream as the previously referred to liquid recycle stream; removing an aqueous liquid stream comprising at least 60 mole percent water from the overhead receiver and passing at least a first portion of the aqueous liquid stream into a steam generation zone wherein by indirect heat exchange against a high temperature fluid the first portion of the aqueous liquid stream is at least partially vaporized to form moderate pressure steam; and passing at least a portion of the moderate pressure steam into the steam-jet ejector as the high pressure motive stream utilized in the ejector to evacuate the overhead receiver.

I claim as my invention:

1. A method of fractionating distillable mixtures which comprises the steps of:
   (a) passing a feed stream comprising water and a mixture of a first and a second distillable hydrocarbonaceous compounds into a fractionation column at a first point, and removing a first product stream comprising the first distillable hydrocarbonaceous compound from the fractionation column at a second lower point;
   (b) effecting a partial condensation of an overhead vapor stream comprising water vapor and the second distillable hydrocarbonaceous compound and which is removed from the fractionation column by admixing the overhead vapor stream with a hereinafter specified liquid recycle stream and by passing the overhead vapor stream through a first condensing zone, and passing the resultant mixed-phase stream into an overhead receiver maintained at a subatmospheric pressure;
   (c) withdrawing an overhead liquid comprising the second distillable hydrocarbonaceous compound and containing less than 10 mole percent water from the overhead receiver, passing a first portion of the overhead liquid into the fractionation column as reflux and removing a second portion of the overhead liquid as a second product stream;
   (d) passing a first vapor stream comprising water and the second distillable hydrocarbonaceous compound from the overhead receiver to the suction inlet of a steam-jet ejector operated at conditions effective to maintain the subatmospheric pressure in the overhead receiver and thereby forming an ejector effluent stream comprising the second distillable hydrocarbonaceous compound and steam;
   (e) condensing at least a portion of the ejector effluent stream by passage through a second condensing zone;
   (f) passing the ejector effluent stream into a vapor-liquid separation zone maintained at conditions effective to separate the ejector effluent stream into a second vapor stream comprising water and a condensate liquid stream comprising water and the second distillable hydrocarbonaceous compound;
   (g) admixing the condensate liquid stream into the overhead vapor stream as the liquid recycle stream of step (b);
   (h) removing an aqueous liquid stream comprising at least 60 mole percent water from the overhead receiver and passing at least a first portion of the aqueous liquid stream into a steam generation zone wherein by indirect heat exchange against a high temperature fluid the first portion of the aqueous liquid stream is at least partially vaporized to form moderate pressure steam; and,
   (i) passing at least a portion of the moderate pressure steam into the steam-jet ejector of step (d) as the motive stream utilized in the ejector.

2. The method of claim 1 further characterized in that a liquid water stream is removed from the steam generation zone, combined with the condensate liquid stream and then passed into the overhead receiver.

3. The method of claim 2 further characterized in that the feed stream passed into the fractionation column is a rich solvent stream, the first distillable hydrocarbonaceous compound is a solvent selective for aromatic hydrocarbons, and the second distillable hydrocarbonaceous compound is an aromatic hydrocarbon chosen from the group consisting of benzene, toluene, xylene and ethylbenzene.

4. The method of claim 3 further characterized in that the solvent is of the sulfolane type.

5. The method of claim 1 further characterized in that a second portion of the moderate pressure steam is passed into a lower portion of the fractionation column.

6. The method of claim 5 further characterized in that the feed stream passed into the fractionation column is a rich solvent stream, the first distillable hydrocarbonaceous compound is a solvent selective for aromatic hydrocarbons, and the second distillable hydrocarbonaceous compound is an aromatic hydrocarbon chosen from the group consisting of benzene, toluene, xylene and ethylbenzene.

7. The method of claim 6 further characterized in that the solvent is of the sulfolane type.

* * * * *